(12) United States Patent
Fallin et al.

(10) Patent No.: US 9,687,221 B2
(45) Date of Patent: Jun. 27, 2017

(54) METHOD OF ANCHORING A SUTURE (71) Applicant: VentureMD Innovations, LLC, Logan, UT (US)

(72) Inventors: T. Wade Fallin, Hyde Park, UT (US); M. Mary Sinnott, Logan, UT (US)

(73) Assignee: Venture MD Innovations, LLC, Logan, UT (US)

( * ) Notice: Subject to any disclaimer, the term of this patent is extended or adjusted under 35 U.S.C. 154(b) by 85 days.

(21) Appl. No.: 14/179,438

(22) Filed: Feb. 12, 2014

(65) Prior Publication Data

US 2014/0228866 A1 Aug. 14, 2014

Related U.S. Application Data

(60) Provisional application No. 61/764,485, filed on Feb. 13, 2013.

(51) Int. Cl.
*A61B 17/04* (2006.01)

(52) U.S. Cl.
CPC ...... *A61B 17/0401* (2013.01); *A61B 17/0485* (2013.01); *A61B 2017/044* (2013.01); *A61B 2017/0409* (2013.01); *A61B 2017/0445* (2013.01)

(58) Field of Classification Search
CPC ............ A61B 17/0401; A61B 17/0469; A61B 2017/044; A61B 2017/0404; A61B 2017/0414; A61B 2017/0458; A61B 2017/0469; A61B 2017/0445; A61B 2017/0451; A61B 2017/0453; A61B 2017/0454; A61B 2017/0456; A61B 2017/0403; A61B 2017/0408; A61B 2017/0409; A61B 2017/0411; A61B 2017/0412; A61B 2017/0416; A61B 2017/0417; A61B 2017/0419; A61B 2017/042; A61B 2017/0422; A61B 2017/0424; A61B 2017/0425; A61B 2017/0427; A61B 2017/0429; A61B 2017/043; A61B 2017/0432; A61B 2017/0433; A61B 2017/0435; A61B 2017/0437; A61B 2017/0438; A61B 2017/0443; A61B 2017/0459; A61B 2017/0461; A61B 2017/0462;
(Continued)

(56) References Cited

U.S. PATENT DOCUMENTS

| 1,583,271 A | 5/1926 | Biro |
| 1,856,721 A | 5/1932 | Nagelmann |
| 4,441,497 A | 4/1984 | Paudler |

(Continued)

FOREIGN PATENT DOCUMENTS

| EP | 2070481 A1 | 6/2009 |
| WO | WO 2010/132310 A1 | 11/2010 |

(Continued)

OTHER PUBLICATIONS

"Arthrex PassPort Button Cannula" (2011) Arthrex, Inc., 6pgs. www.arthrex.com.
(Continued)

*Primary Examiner* — Jonathan Miles
*Assistant Examiner* — Kankindi Rwego (57) ABSTRACT

Devices and methods are presented for securing a suture to facilitate a surgical procedure.

16 Claims, 11 Drawing Sheets

(58) Field of Classification Search
CPC ..... A61B 2017/0464; A61F 2002/0876; A61F 2002/0882; A61F 2002/0888
See application file for complete search history.

(56) References Cited

U.S. PATENT DOCUMENTS

| | | |
|---|---|---|
| 4,622,960 A | 11/1986 | Tam |
| 4,672,957 A | 6/1987 | Hourahane |
| 4,890,615 A | 1/1990 | Caspari et al. |
| 4,898,156 A | 2/1990 | Gatturna |
| 5,152,790 A | 10/1992 | Rosenberg et al. |
| 5,176,682 A * | 1/1993 | Chow ............... A61B 17/0401 606/139 |
| 5,250,055 A | 10/1993 | Moore et al. |
| 5,254,126 A | 10/1993 | Filipi et al. |
| 5,342,369 A | 8/1994 | Harryman, II |
| 5,350,380 A | 9/1994 | Goble et al. |
| 5,354,300 A | 10/1994 | Goble et al. |
| 5,417,701 A | 5/1995 | Holmes |
| 5,439,467 A | 8/1995 | Benderev et al. |
| 5,454,823 A | 10/1995 | Richardson et al. |
| 5,464,427 A | 11/1995 | Curtis |
| 5,480,403 A | 1/1996 | Lee |
| 5,486,197 A | 1/1996 | Le |
| 5,544,664 A | 8/1996 | Benderev et al. |
| 5,545,180 A | 8/1996 | Le |
| 5,562,683 A | 10/1996 | Chan |
| 5,562,684 A | 10/1996 | Kammerer |
| 5,562,687 A | 10/1996 | Chan |
| 5,569,306 A | 10/1996 | Thal |
| 5,572,770 A | 11/1996 | Boden |
| 5,575,801 A | 11/1996 | Habermeyer et al. |
| 5,584,839 A | 12/1996 | Gieringer |
| 5,601,562 A | 2/1997 | Wolf et al. |
| 5,624,446 A | 4/1997 | Harryman, II |
| 5,649,963 A | 7/1997 | McDevitt |
| 5,681,333 A | 10/1997 | Burkhart et al. |
| 5,683,419 A | 11/1997 | Thal |
| 5,688,284 A | 11/1997 | Chervitz et al. |
| 5,700,266 A | 12/1997 | Harryman, II |
| 5,702,397 A | 12/1997 | Goble et al. |
| 5,709,708 A | 1/1998 | Thal |
| 5,730,747 A | 3/1998 | Ek et al. |
| 5,746,754 A | 5/1998 | Chan |
| 5,755,728 A | 5/1998 | Maki |
| 5,776,151 A | 7/1998 | Chan |
| 5,800,447 A | 9/1998 | Wenstrom, Jr. |
| 5,824,009 A | 10/1998 | Fukuda et al. |
| 5,868,762 A | 2/1999 | Cragg et al. |
| 5,891,150 A | 4/1999 | Chan |
| 5,891,168 A | 4/1999 | Thal |
| 5,895,425 A | 4/1999 | Grafton et al. |
| 5,899,921 A | 5/1999 | Caspari et al. |
| 5,906,624 A | 5/1999 | Wenstrom, Jr. |
| 5,935,129 A | 8/1999 | McDevitt |
| 5,947,982 A | 9/1999 | Duran |
| 5,948,000 A | 9/1999 | Larsen |
| 5,964,783 A | 10/1999 | Grafton et al. |
| 6,024,758 A | 2/2000 | Thal |
| 6,045,574 A | 4/2000 | Thal |
| 6,053,916 A | 4/2000 | Moore |
| 6,099,538 A | 8/2000 | Moses et al. |
| 6,120,511 A | 9/2000 | Chan |
| 6,143,017 A | 11/2000 | Thal |
| 6,156,039 A | 12/2000 | Thal |
| 6,183,479 B1 | 2/2001 | Tormala |
| 6,290,711 B1 | 9/2001 | Caspari |
| 6,368,355 B1 | 4/2002 | Chan |
| 6,387,129 B2 | 5/2002 | Rieser et al. |
| 6,511,487 B1 | 1/2003 | Oren et al. |
| 6,514,274 B1 | 2/2003 | Boucher |
| 6,517,542 B1 | 2/2003 | Papay et al. |
| 6,524,317 B1 | 2/2003 | Ritchart et al. |
| 6,527,795 B1 | 3/2003 | Lizardi |
| 6,544,281 B2 | 4/2003 | Elattrache et al. |
| 6,599,295 B1 | 7/2003 | Tornier |
| 6,623,524 B2 | 9/2003 | Schmieding |
| 6,629,984 B1 | 10/2003 | Chan |
| 6,638,283 B2 | 10/2003 | Thal |
| 6,641,597 B2 | 11/2003 | Burkhart et al. |
| 6,652,561 B1 | 11/2003 | Tran |
| 6,656,183 B2 | 12/2003 | Colleran et al. |
| 6,666,877 B2 | 12/2003 | Morgan et al. |
| 6,692,516 B2 | 2/2004 | West, Jr. et al. |
| 6,723,107 B1 | 4/2004 | Skiba et al. |
| 6,743,233 B1 | 6/2004 | Baldwin et al. |
| 6,770,076 B2 | 8/2004 | Foerster |
| 6,855,157 B2 | 2/2005 | Foerster |
| 6,932,826 B2 | 8/2005 | Chan |
| 6,955,678 B2 | 10/2005 | Gabriel et al. |
| 6,958,067 B2 | 10/2005 | Whittaker et al. |
| 6,984,237 B2 | 1/2006 | Hatch et al. |
| 6,986,781 B2 | 1/2006 | Smith |
| 6,991,636 B2 | 1/2006 | Rose |
| 6,994,725 B1 | 2/2006 | Goble |
| 7,033,364 B1 | 4/2006 | Walters et al. |
| 7,063,724 B2 | 6/2006 | Re et al. |
| 7,077,863 B2 | 7/2006 | Schmieding et al. |
| 7,108,700 B2 | 9/2006 | Chan |
| 7,112,208 B2 | 9/2006 | Morris et al. |
| 7,175,632 B2 | 2/2007 | Singhatat et al. |
| 7,201,756 B2 | 4/2007 | Ross et al. |
| 7,247,164 B1 | 7/2007 | Ritchart et al. |
| 7,309,337 B2 | 12/2007 | Colleran et al. |
| 7,329,272 B2 | 2/2008 | Burkhart et al. |
| 7,341,592 B1 | 3/2008 | Walters et al. |
| 7,377,926 B2 | 5/2008 | Topper et al. |
| 7,381,212 B2 | 6/2008 | Topper et al. |
| 7,399,302 B2 | 7/2008 | Goble et al. |
| 7,465,308 B2 | 12/2008 | Sikora et al. |
| 7,517,357 B2 | 4/2009 | Abrams |
| 7,527,648 B2 | 5/2009 | May |
| 7,530,999 B2 * | 5/2009 | Clark ............... A61B 17/1615 623/13.12 |
| 7,569,059 B2 | 8/2009 | Cerundolo |
| 7,585,305 B2 | 9/2009 | Dreyfuss |
| 7,585,311 B2 | 9/2009 | Green et al. |
| 7,594,917 B2 | 9/2009 | Whittakter et al. |
| 7,608,084 B2 | 10/2009 | Oren et al. |
| 7,625,386 B2 | 12/2009 | Abe et al. |
| 7,655,011 B2 | 2/2010 | Whittaker et al. |
| 7,713,286 B2 | 5/2010 | Singhatat |
| 7,749,237 B2 | 7/2010 | Chan |
| 7,771,441 B2 | 8/2010 | Cerundolo |
| 7,803,173 B2 | 9/2010 | Burkhart et al. |
| 7,833,230 B2 | 11/2010 | Cerundolo |
| 7,833,244 B2 | 11/2010 | Cerundolo |
| 7,837,710 B2 | 11/2010 | Lombardo et al. |
| 7,867,251 B2 | 1/2011 | Colleran et al. |
| 7,875,058 B2 * | 1/2011 | Holmes, Jr. ........ A61B 17/0401 606/232 |
| 7,879,046 B2 | 2/2011 | Weinert et al. |
| 7,879,048 B2 | 2/2011 | Bain et al. |
| 7,883,519 B2 | 2/2011 | Oren et al. |
| 7,887,564 B2 | 2/2011 | Boehringer et al. |
| 7,931,657 B2 | 4/2011 | Walters et al. |
| 7,938,847 B2 | 5/2011 | Fanton et al. |
| 7,942,914 B2 | 5/2011 | Cerundolo |
| 7,955,341 B2 | 6/2011 | Cerundolo |
| 7,963,972 B2 | 6/2011 | Foerster et al. |
| 7,976,565 B1 | 7/2011 | Meridew |
| 7,981,140 B2 | 7/2011 | Burkhart et al. |
| 7,988,697 B2 | 8/2011 | Miller et al. |
| 7,993,369 B2 | 8/2011 | Dreyfuss |
| 8,038,652 B2 | 10/2011 | Morrison et al. |
| 8,043,308 B2 | 10/2011 | Bittenson |
| 8,062,295 B2 | 11/2011 | McDevitt |
| 8,100,942 B1 | 1/2012 | Green et al. |
| 8,105,343 B2 | 1/2012 | White et al. |
| 8,109,966 B2 | 2/2012 | Ritchart et al. |
| 8,109,969 B1 | 2/2012 | Green et al. |
| 8,137,360 B2 | 3/2012 | Whittaker et al. |
| 8,137,381 B2 | 3/2012 | Foerster |
| 8,147,505 B2 | 4/2012 | Delli-Santi |

(56) References Cited

U.S. PATENT DOCUMENTS

| | | |
|---|---|---|
| 8,177,796 B2 | 5/2012 | Akyuz et al. |
| 8,202,295 B2 | 6/2012 | Kaplan |
| 8,202,297 B2 | 6/2012 | Burkhart |
| 8,231,653 B2 | 7/2012 | Dreyfuss |
| 8,262,675 B2 | 9/2012 | Cropper |
| 8,267,964 B2 | 9/2012 | Green et al. |
| 8,282,643 B2 | 10/2012 | Dross |
| 8,317,829 B2 | 11/2012 | Foerster |
| 8,317,862 B2 | 11/2012 | Troger |
| 8,409,225 B2 | 4/2013 | Bull |
| 8,444,674 B2 | 5/2013 | Kaplan |
| 8,491,595 B2 | 7/2013 | Volpi |
| 8,506,596 B2 | 8/2013 | Stone |
| 8,518,091 B2 | 8/2013 | McDevitt |
| 8,540,737 B2 | 9/2013 | Chudik |
| 8,597,328 B2 | 12/2013 | Cauldwell |
| 8,663,280 B2 | 3/2014 | Kaplan |
| 8,740,913 B2 | 6/2014 | Schneider |
| 8,747,469 B2 | 6/2014 | Wang |
| 8,790,370 B2 | 7/2014 | Spenciner |
| 8,808,326 B2 | 8/2014 | Gagliano |
| 8,961,576 B2 | 2/2015 | Hodge |
| 8,986,347 B2 | 3/2015 | Housman |
| 9,011,466 B2 | 4/2015 | Adams et al. |
| 9,023,083 B2 | 5/2015 | Foerster |
| 9,034,014 B2 | 5/2015 | Catania |
| 9,149,268 B2 | 10/2015 | Graul |
| 2001/0016747 A1 | 8/2001 | Romano et al. |
| 2001/0037119 A1 | 11/2001 | Schmieding |
| 2001/0049529 A1 | 12/2001 | Cachia et al. |
| 2001/0049536 A1 | 12/2001 | Chan et al. |
| 2002/0111653 A1 | 8/2002 | Foerster |
| 2002/0147456 A1 | 10/2002 | Diduch et al. |
| 2002/0165546 A1 | 11/2002 | Goble et al. |
| 2002/0188298 A1* | 12/2002 | Chan ............... A61F 2/0811 623/13.11 |
| 2003/0195528 A1 | 10/2003 | Ritchart |
| 2003/0195563 A1 | 10/2003 | Foerster |
| 2003/0229362 A1 | 12/2003 | Chan et al. |
| 2004/0098051 A1 | 5/2004 | Fallin |
| 2004/0116843 A1 | 6/2004 | Chan |
| 2004/0133239 A1 | 7/2004 | Singhatat |
| 2004/0172062 A1 | 9/2004 | Burkhart |
| 2004/0193172 A1 | 9/2004 | Ross et al. |
| 2004/0193187 A1 | 9/2004 | Boehringer et al. |
| 2004/0267317 A1 | 12/2004 | Higgins |
| 2005/0055052 A1 | 3/2005 | Lombardo et al. |
| 2005/0075668 A1 | 4/2005 | Lizardi |
| 2005/0245932 A1 | 11/2005 | Fanton et al. |
| 2005/0277986 A1 | 12/2005 | Foerster et al. |
| 2005/0283156 A1 | 12/2005 | Schmieding et al. |
| 2006/0004410 A1 | 1/2006 | Nobis et al. |
| 2006/0074438 A1 | 4/2006 | Chan |
| 2006/0079904 A1 | 4/2006 | Thal |
| 2006/0106422 A1 | 5/2006 | Del Rio et al. |
| 2006/0149258 A1 | 7/2006 | Sousa |
| 2006/0235413 A1 | 10/2006 | Denham et al. |
| 2006/0241658 A1 | 10/2006 | Cerundolo |
| 2006/0247642 A1 | 11/2006 | Stone et al. |
| 2006/0276841 A1 | 12/2006 | Barbieri et al. |
| 2007/0088362 A1 | 4/2007 | Bonutti |
| 2007/0112352 A1 | 5/2007 | Sorensen et al. |
| 2007/0123887 A1 | 5/2007 | Hirt et al. |
| 2007/0173865 A1 | 7/2007 | Oren et al. |
| 2007/0179510 A1 | 8/2007 | Stone |
| 2007/0191849 A1 | 8/2007 | Elatrrache et al. |
| 2007/0203498 A1 | 8/2007 | Gerber et al. |
| 2007/0219558 A1 | 9/2007 | Deutsch |
| 2007/0260259 A1 | 11/2007 | Fanton et al. |
| 2007/0270854 A1 | 11/2007 | Li et al. |
| 2008/0004659 A1 | 1/2008 | Burkhart et al. |
| 2008/0009904 A1 | 1/2008 | Bourque et al. |
| 2008/0033486 A1 | 2/2008 | Whittaaker et al. |
| 2008/0077161 A1 | 3/2008 | Kaplan |
| 2008/0125815 A1 | 5/2008 | Heaven |
| 2008/0154314 A1* | 6/2008 | McDevitt ............... A61B 17/8095 606/304 |
| 2008/0208253 A1 | 8/2008 | Dreyfuss et al. |
| 2008/0262544 A1 | 10/2008 | Burkhart et al. |
| 2008/0275453 A1 | 11/2008 | Lafosse et al. |
| 2008/0287992 A1 | 11/2008 | Tornier |
| 2008/0300629 A1 | 12/2008 | Surti |
| 2009/0018581 A1 | 1/2009 | Anderson |
| 2009/0036905 A1 | 2/2009 | Schmieding |
| 2009/0062819 A1 | 3/2009 | Burkhart et al. |
| 2009/0076544 A1 | 3/2009 | DiMatteo |
| 2009/0088708 A1 | 4/2009 | Boehringer et al. |
| 2009/0099598 A1 | 4/2009 | McDevitt |
| 2009/0112270 A1 | 4/2009 | Lunn et al. |
| 2009/0157124 A1 | 6/2009 | Ferragamo et al. |
| 2009/0187216 A1 | 7/2009 | Schmieding et al. |
| 2009/0192546 A1 | 7/2009 | Schmieding et al. |
| 2009/0234387 A1 | 9/2009 | Miller et al. |
| 2009/0292312 A1 | 11/2009 | Tochimura et al. |
| 2009/0292321 A1* | 11/2009 | Collette ............... A61F 2/0811 606/303 |
| 2009/0312794 A1 | 12/2009 | Nason |
| 2009/0318959 A1 | 12/2009 | Burkhart et al. |
| 2009/0318960 A1 | 12/2009 | Burkhart |
| 2009/0326579 A1 | 12/2009 | Anderhub et al. |
| 2010/0063542 A1 | 3/2010 | Van Der Burg et al. |
| 2010/0069974 A1 | 3/2010 | Oren et al. |
| 2010/0094355 A1 | 4/2010 | Trenhaile |
| 2010/0100127 A1 | 4/2010 | Trenhaile |
| 2010/0114123 A1 | 5/2010 | Nason |
| 2010/0121337 A1 | 5/2010 | Pandya |
| 2010/0121338 A1 | 5/2010 | Pandya |
| 2010/0121348 A1 | 5/2010 | Van Der Burg et al. |
| 2010/0121349 A1 | 5/2010 | Meier et al. |
| 2010/0121354 A1 | 5/2010 | Pandya |
| 2010/0121375 A1 | 5/2010 | Pandya |
| 2010/0137889 A1 | 6/2010 | Oren et al. |
| 2010/0160962 A1 | 6/2010 | Dreyfuss et al. |
| 2010/0179592 A1 | 7/2010 | Martinek et al. |
| 2010/0198235 A1 | 8/2010 | Pierce et al. |
| 2010/0198258 A1 | 8/2010 | Heaven et al. |
| 2010/0228254 A1 | 9/2010 | Pandya |
| 2010/0249806 A1 | 9/2010 | Oren et al. |
| 2010/0249834 A1 | 9/2010 | Dreyfuss |
| 2010/0292733 A1 | 11/2010 | Hendrickson et al. |
| 2010/0312249 A1 | 12/2010 | Sanders |
| 2010/0318139 A1 | 12/2010 | Beauchamp |
| 2010/0324575 A1 | 12/2010 | Chan |
| 2010/0331881 A1 | 12/2010 | Hart |
| 2011/0009867 A1 | 1/2011 | Oren et al. |
| 2011/0009884 A1 | 1/2011 | Kaplan |
| 2011/0022087 A1 | 1/2011 | Cerundolo |
| 2011/0087245 A1 | 4/2011 | Weinert et al. |
| 2011/0106124 A1 | 5/2011 | Beauchamp |
| 2011/0112550 A1 | 5/2011 | Heaven |
| 2011/0112576 A1 | 5/2011 | Nguyen et al. |
| 2011/0118757 A1 | 5/2011 | Pierce |
| 2011/0118762 A1 | 5/2011 | Dooney, Jr. |
| 2011/0152928 A1 | 6/2011 | Colleran et al. |
| 2011/0208198 A1 | 8/2011 | Anderson |
| 2011/0224726 A1 | 9/2011 | Lombardo |
| 2011/0264140 A1 | 10/2011 | Lizardi et al. |
| 2012/0053626 A1 | 3/2012 | Koepke |
| 2012/0143224 A1 | 6/2012 | Chan |
| 2012/0179199 A1* | 7/2012 | Hernandez ............... A61B 17/0401 606/232 |
| 2012/0209279 A1 | 8/2012 | Snyder |
| 2012/0245634 A1 | 9/2012 | Kaplan |
| 2013/0096611 A1 | 4/2013 | Sullivan |
| 2013/0103083 A1 | 4/2013 | Baird |
| 2013/0123809 A1 | 5/2013 | Murphy et al. |
| 2013/0123840 A1 | 5/2013 | Murphy et al. |
| 2013/0123842 A1 | 5/2013 | Chan et al. |
| 2013/0123843 A1 | 5/2013 | Chan et al. |
| 2013/0144335 A1 | 6/2013 | Sandow |
| 2013/0190871 A1 | 7/2013 | Markarian |
| 2013/0197575 A1 | 8/2013 | Karapetian |
| 2013/0197577 A1 | 8/2013 | Wolf |
| 2013/0197578 A1 | 8/2013 | Gregoire |

(56) References Cited

U.S. PATENT DOCUMENTS

| | | |
|---|---|---|
| 2013/0204299 A1 | 8/2013 | Mantovani et al. |
| 2013/0345711 A1 | 12/2013 | Mehta |
| 2014/0046369 A1 | 2/2014 | Heaven |
| 2014/0114411 A1 | 4/2014 | Baird |
| 2014/0134802 A1 | 5/2014 | Lin |
| 2014/0172016 A1 | 6/2014 | Housman |
| 2014/0303625 A1 | 10/2014 | Sholev |
| 2014/0343605 A1 | 11/2014 | Lunn |
| 2014/0364905 A1 | 12/2014 | Lunn |
| 2015/0119937 A1 | 4/2015 | Lunn |
| 2015/0150551 A1 | 6/2015 | Paulk |
| 2015/0196388 A1 | 7/2015 | Housman |

FOREIGN PATENT DOCUMENTS

| | | |
|---|---|---|
| WO | WO 2011/008607 A1 | 1/2011 |
| WO | WO 2012/007941 A2 | 1/2012 |
| WO | WO 2013/027209 A1 | 2/2013 |
| WO | WO 2013/027210 A1 | 2/2013 |

OTHER PUBLICATIONS

"Arthroscopic Shoulder Repair Using the Smith & Nephew Footprint PK Suture Anchor" (2008) Smith & Nephew, Inc., 12pgs.
"CurvTek Bone Tunneling System" (2000) Arthrotek, Inc., 6pgs.
"The OPUS® AutoCuff® System Featuring SpeeScrew™ for Rotator Cuff Repair" (2009) Arthrocare Corporation, 8pgs.
ArthroCare Sports Medicine International, Products: SpeedStitch MagnumWire Suture Cartridges, (3ea: white & co-braid), http://www.arthrocaresportsmedicine.com/products/view/435 Sep. 24, 2012, 1pg.
ArthroCare Sports Medicine International, Products: SpeedStitch Suturing Device, http://www.arthrocaresportsmedicine.com/products/view/431 Sep. 24, 2012, 1pg.
Baums, et al. "Tendon-bone contact pressure and biomechanical evaluation of a modified suture-bridge technique for rotator cuff repair" Knee Surg Sports Traumatol Arthrosc (2010) 18:992-998.
Dermirhan, et al. "Current Concept: Arthroscopic Transosseous Equivalent Suture Bridge Rotator Cuff Repair" (2012) 109-115, Springer-Verlag Berlin Heidelberg.
Lorbach and Tompkings "Rotator Cuff: Biology and Current Arthroscopic Techniques" Knee Surg Sports Traumatol Arthrosc, Springer-Verlag, published online: Jan. 21, 2012, 9pgs.
Maguire, et al. "Biomechanical Evaluation of Four Different Transosseous-equivalent/suture Bridge Rotator Cuff Repairs" Knee Surg Sports Traumatol Arhtrosc (2011) 19:1582-1587.
Park, et al. "Part I: Footprint Contact Characteristics for a Transosseous-equivalent Rotator Cuff Repair Technique Compared with a Double-row Repair Technique" J.Shoulder Elbow Surg (2007) 16(4):461-468.
Upper Limb Surgery Info., Adelaide—Wakefield Orthopaedic Clinic, SA, Jan. 30, 2012, 4pgs. http://www.woc.com.au/upper-limb-research.html.
VERSALOK™ The Next Generation in Rotator Cuff Repair, (2007) DePuy Mitek, Inc., www.depuymitek.com, 18pgs.
Multifix's PEEK 5.5mm and 6.5mm Knotless Implants Technique Guide, ArthroCare Corporation, www.smith-nephew.com, Jul. 2015, 8 pp.
Multifix PEEK Knotless Fixation Implants, ArthroCare Corporation, www.smith-nephew.com, Aug. 2015, 6 pp.
Achilles Speedbridge Surgical Technique, Arthrex, Inc., www.arthrex.com, 2013, 6 pp.
Achilles Suturebridge Surgical Technique, Arthrex, Inc., www.arthrex.com, 2014, 6 pp.
Massive Rotator Cuff Repair and Augmentation using the Speedbridge and ArthroFlex Dermal Matrix Surgical Technique, Arthrex, Inc., www.arthrex.com, 2012 4 pp.
Arthrex is Reaching New Heights in Rotator Cuff Repair, Arthrex, Inc. www.arthrex.com, 2007, 8 pp.
Speedbridge and SpeedFix Knotless Rotator Cuff Repair using the SwiveLock C and FiberTape Surgical Technique, Arthrex, Inc. www.arthrex.com, 2013, 8 pp.
SutureBridge Double Row Rotator Cuff Repair Surgical Technique, Arthrex, Inc. www.arthrex.com, 2013, 6 pp.
Quattro Shoulder System—Innovative Rotator Cuff Solutions, Cayenne Medical, Inc., www.cayennemedical.com, 6 pp.
Shoulder Restoration System—PopLok Knotless Suture Anchor Surgical Technique, ConMed Linvatec, www.linvatec.com, 2013, 8 pp.
The Next Generation in Rotator Cuff Repair, DePuy Mitek, Inc., www.depuymitek.com, 2007, 18 pp.
Footprint PK Suture Anchor, Arthroscopic Shoulder Repair Using the Smith & Nephew Footprint PK Suture Anchor Technique Guide, Smith & Nephew, Inc., www.smith-nephew.com, Apr. 2008, 12 pp.
Mall, Nathan A., et al. "Transosseous-Equivalent Rotator Cuff Repair: A Systematic Review on the Biomechanical Importance of Tying the Medial Row", The Journal of Arthroscopic and Related Surgery, vol. 29, No. 2, Feb. 2013, pp. 377-386.
Sharc-FT and Taylor Stitcher Transosseus Devices for Fast Rotator Cuff Repair Surgical Technique, NCS Lab Medical Devices Factory, 12 pp.
Comprehensive Product Offerings for Your Rotator Cuff Repair, Smith&Nephew, Inc., www.smith-nephew.com, Jul. 2015, 12 pp.
OPUS AutoCuff, Magnum X Knotless Fixation Implant with Independent Tensioning, ArthroCare Sports Medicine, arthrocaresportsmedicine.com, 2009, 2 pp.
The OPUS TwinLock Knotless Fixation System, ArthroCare Sports Medicine, arthrocaresportsmedicine.com, 2010, 2 pp.
The OPUS AutoCuff System for Rotator Cuff Repair, ArthroCare Sports Medicine, arthrocaresportsmedicine.com, 2006, 8 pp.
BioRaptor—Knotless Suture Anchor, Smith&Nephew, Inc., www.smith-nephew.com, Apr. 2010, 6 pp.
Footprint PK Arthroscopic Shoulder Repair Using the Smith &Nephew Footprint PK Suture Anchor Technique Guide, Smith &Nephew, Inc., www.smith-nephew.com, Apr. 2008, 12 pp.
CinchLock SS (Sports Sheath) Knotless Labrum Restoration Surgical Technique, Pivot Medical, Inc., 6 pp.
ReelX STT Knotless Anchor System, Stryker, www.stryker.com, 2010, 4 pp.
Dr. S.D. Gerber Double Row Method Surgical Technique, Stryker, www.stryker.com, 2010, 12 pp.
ArthroTunneler TunnelPro System Transosseous Rotator Cuff Repair, Tornier, Inc., www.tornier.com, 2012, 6 pp.
Quickdraw Knotless Suture Anchor System Surgical Technique, ArthroCare Corporation, www.arthrocare.com, 2011, 28 pp.
European Search Report for EP 12846903.8, dated Jun. 25, 2015, 7 pp.
International Search Report and Written Opinion for PCT/US2012/064669, dated Nov. 12, 2012; 14 pp.

* cited by examiner

METHOD OF ANCHORING A SUTURE

CROSS-REFERENCE TO RELATED APPLICATIONS

This application claims the benefit of U.S. Provisional Application No. 61/764,485, filed Feb. 13, 2013, which is hereby incorporated by reference.

FIELD OF THE INVENTION

The invention relates to methods for anchoring sutures such as for anchoring a suture to a bone in an orthopedic surgical procedure.

BACKGROUND

Various conditions affecting a patient may require surgical intervention involving anchoring a suture for example to repair or reconstruct soft tissue or to connect adjacent bony structures.

SUMMARY

The present invention provides devices and methods for securing a suture to facilitate a surgical procedure.

In one aspect of the invention, a method of securing first and second suture limbs relative to a bone, includes passing first and second suture limbs through a bone tunnel; passing the first suture limb through a cannulated anchor; inserting the anchor into the bone tunnel to trap the second suture limb between the anchor and bone tunnel in interference relationship; and securing the first suture limb.

In another aspect of the invention, a method of tethering first and second bones together, includes anchoring a first suture anchor to the first bone; passing a suture from the first suture anchor through a bone tunnel in the second bone; and inserting a second suture anchor into the bone tunnel in the second bone to secure the suture between the second suture anchor and bone tunnel in interference relationship.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

FIGS. 1-4 depict a cannulated interference anchor 100. The anchor 100 includes an elongated body 102 extending between a proximal end 104 and a distal end 106 along an axis 108. An axial passage 110 extends longitudinally through the body between the proximal and distal ends 104, 106. Optional fixation projections 112 extend radially outwardly from the body 102. In the illustrative example of FIGS. 1-4 the anchor 100 is an interference screw having a coaxial bore and a helical thread spirally about the outside of the body. The axial passage 110 has a non-circular driver engaging profile 114. For example the profile 114 may have at least one flat side and is preferably polygonal. In the illustrative example of FIGS. 1-4 the profile is hexagonal.

Figure 1:
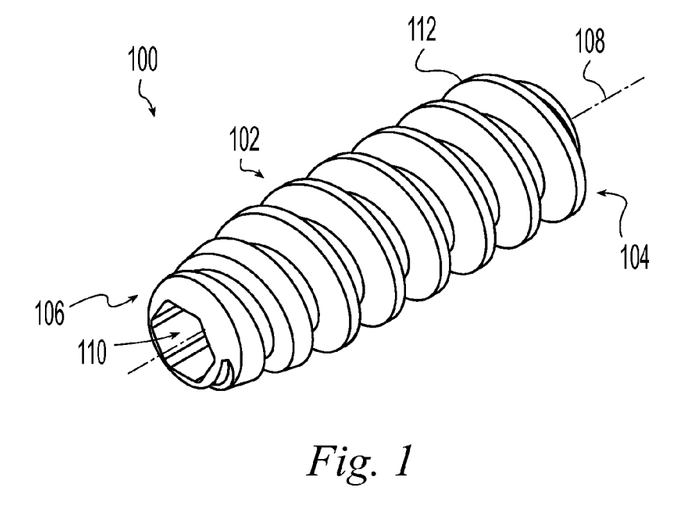
FIG. 1 is a perspective view of an illustrative anchor useable with the method of the present invention.
Figure 2:
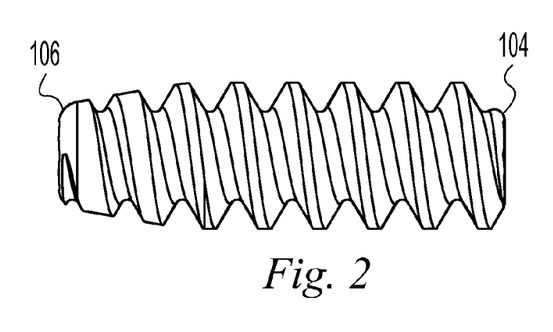
FIG. 2 is a front elevation view of the anchor of FIG. 1.
Figure 3:
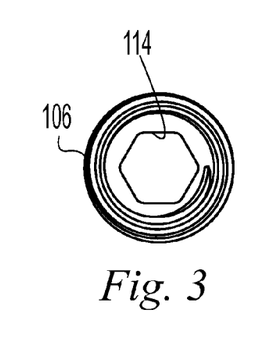
FIG. 3 is a left side elevation view of the anchor of FIG. 1.
Figure 4:
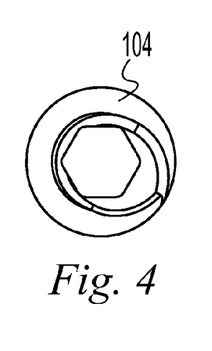
FIG. 4 is a right side elevation view of the anchor of FIG. 1.
Figure 5:
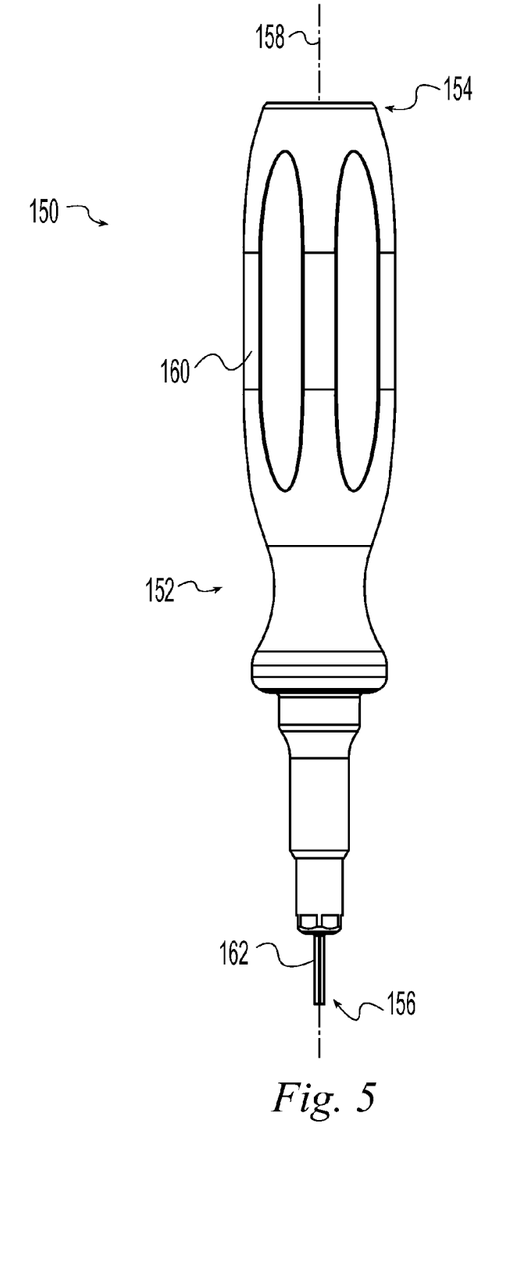
FIG. 5 is a front elevation view of an illustrative driver useable with the anchor of FIG. 1.

FIG. 5 depicts a driver 150 useable with the anchor of FIGS. 1-4. The driver 150 includes an elongated body 152 extending between a proximal end 154 and a distal end 156 along an axis 158. The body includes a handle 160 near the proximal end and an anchor engaging shaft 162 near the distal end. The shaft 162 has a profile complementary to the anchor passage 110 profile and is receivable in the anchor passage 110 in axial sliding relationship for transmitting torque to the anchor 100. An axial passage extends longitudinally through the driver 150 between the proximal and distal ends 154, 156. In the illustrative example of FIG. 5, the screw engaging shaft is hexagonal.

Figure 6:
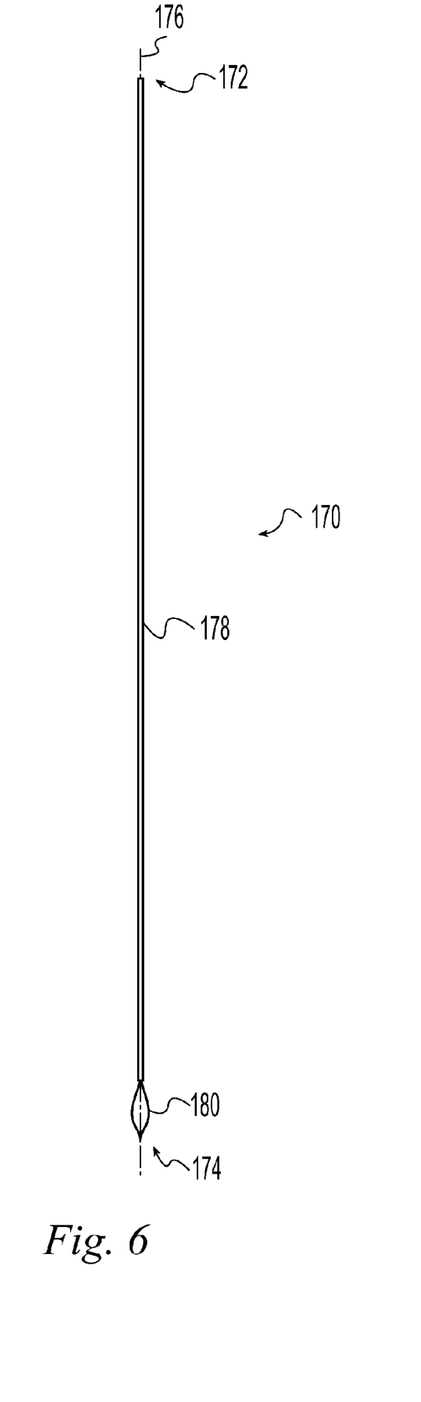
FIG. 6 is a front elevation view of an illustrative suture threader useable with the anchor and driver of FIGS. 1 and 5.

FIG. 6 depicts an elongated suture threader 170 extending between a proximal end 172 and a distal end 174 along an axis 176. The threader 170 includes a shaft 178 and a collapsible loop 180 affixed at the distal end of the shaft.

Figure 7:
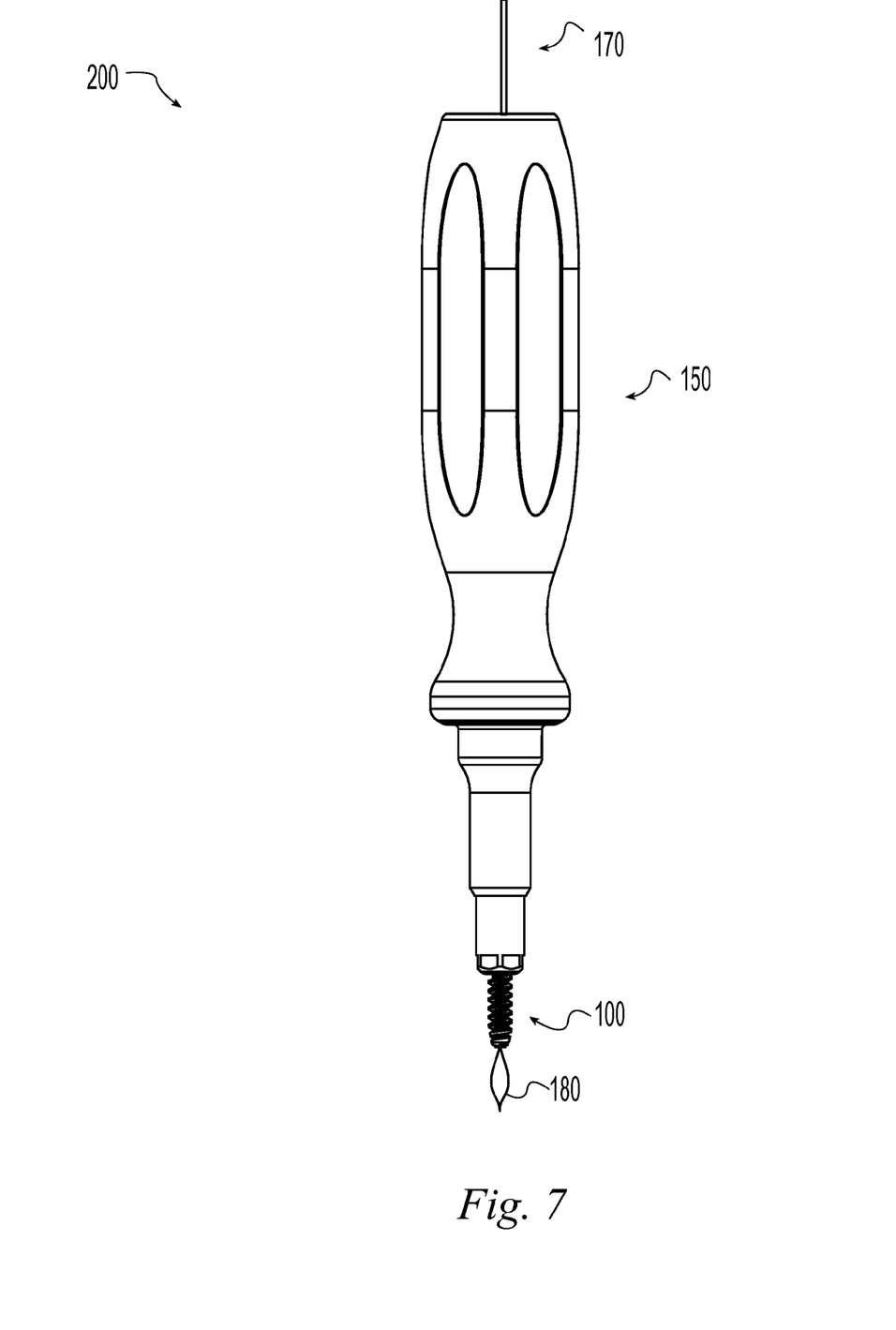
FIG. 7 is a front elevation view of the anchor of FIG. 1, driver of FIG. 5, and threader of FIG. 6 assembled for use.

FIG. 7 depicts the anchor 100, driver 150, and threader 170 assembled into an anchor/driver assembly 200 as they would be prepared for surgery. The anchor 100 is coaxially mounted on the driver shaft 162 and the threader 170 is inserted through the axial passage in the driver 150 so that the loop 180 extends out of the driver and anchor past the distal end.

Figure 8:
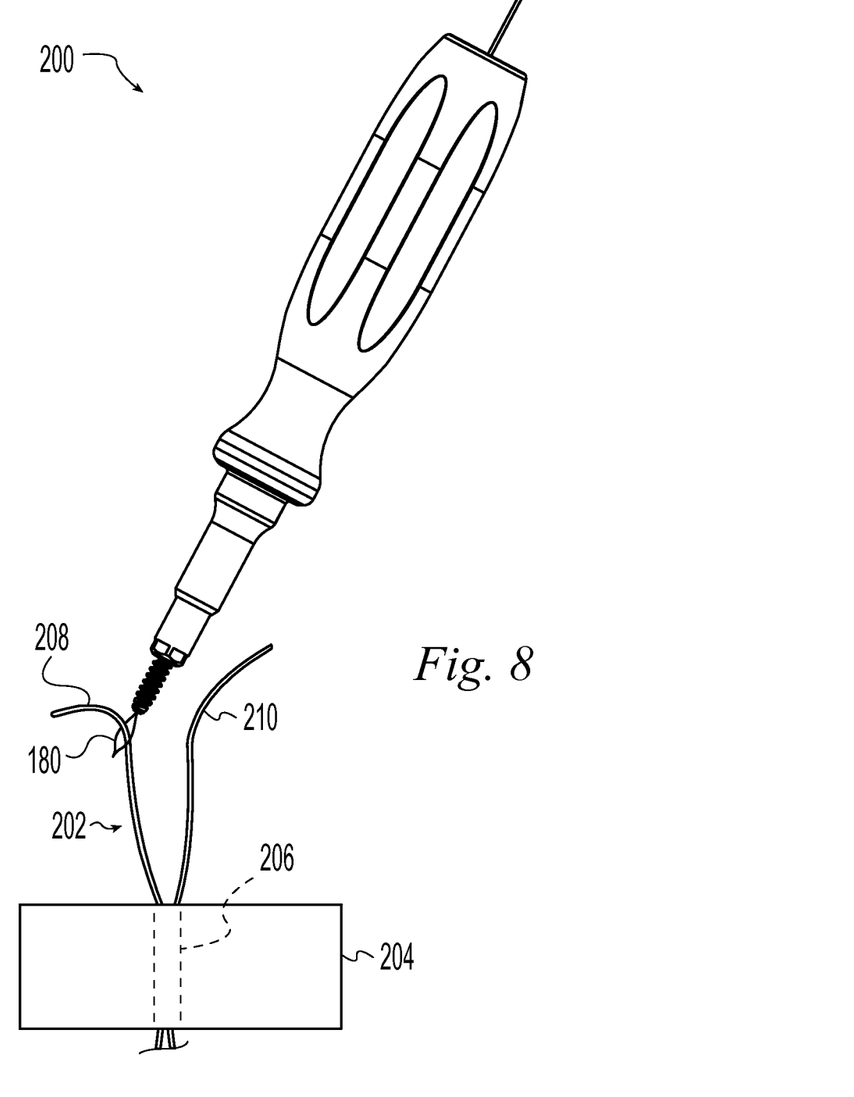
FIGS. 8 and 9 are front elevation views illustrating steps in a method according to the present invention.

FIG. 8 depicts a suture 202 that is to be attached to a bone 204. The suture 202 extends through a tunnel 206 in the bone 204. The devices and methods shown may be used with any number of sutures. In the illustrative example of FIG. 8, first and second suture limbs 208 and 210 extend from the bone tunnel. The first suture limb 208 is placed through the loop 180 of the threader 170 in preparation for threading the first limb 208 through the anchor/driver assembly 200.

Figure 9:
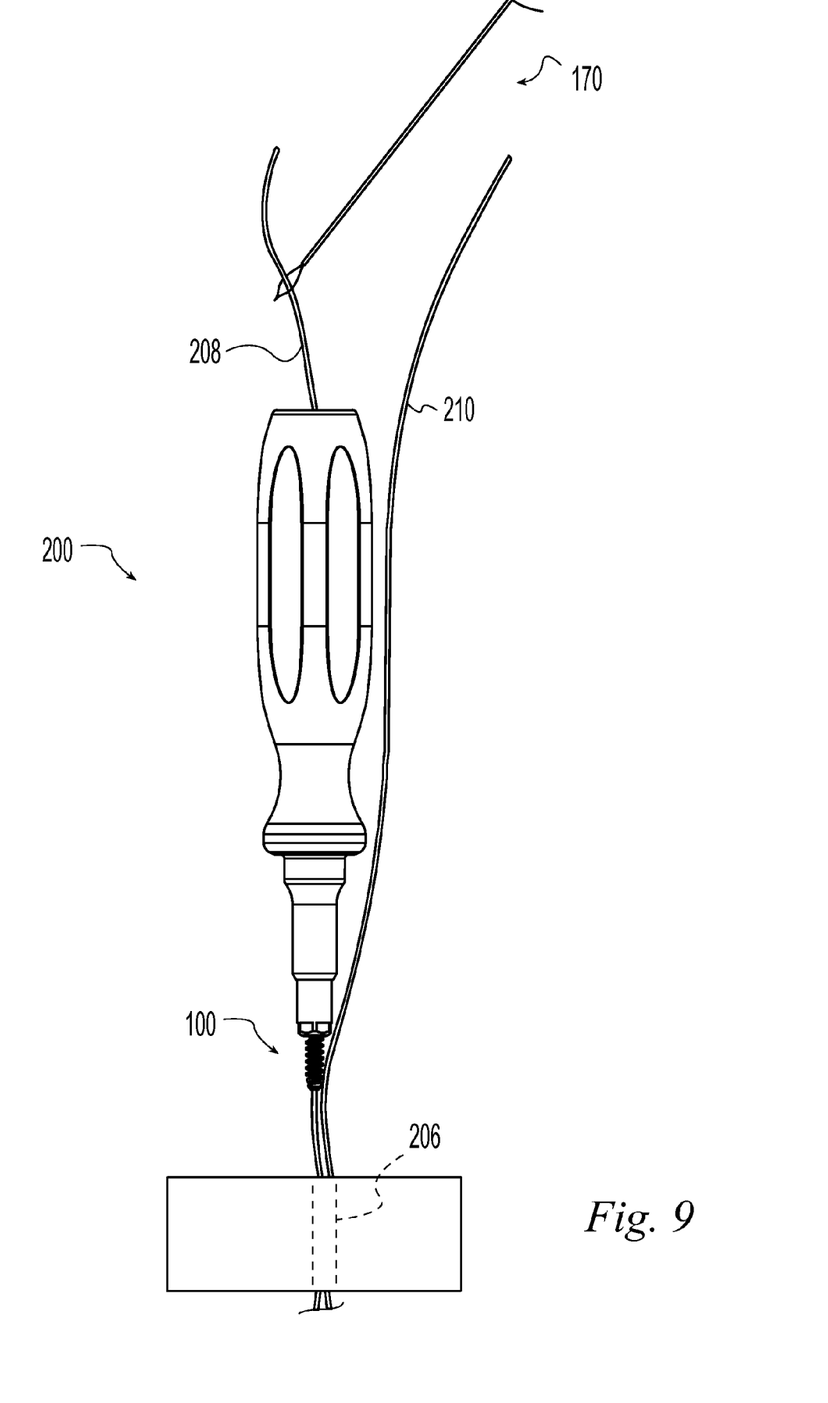
Figure 10:
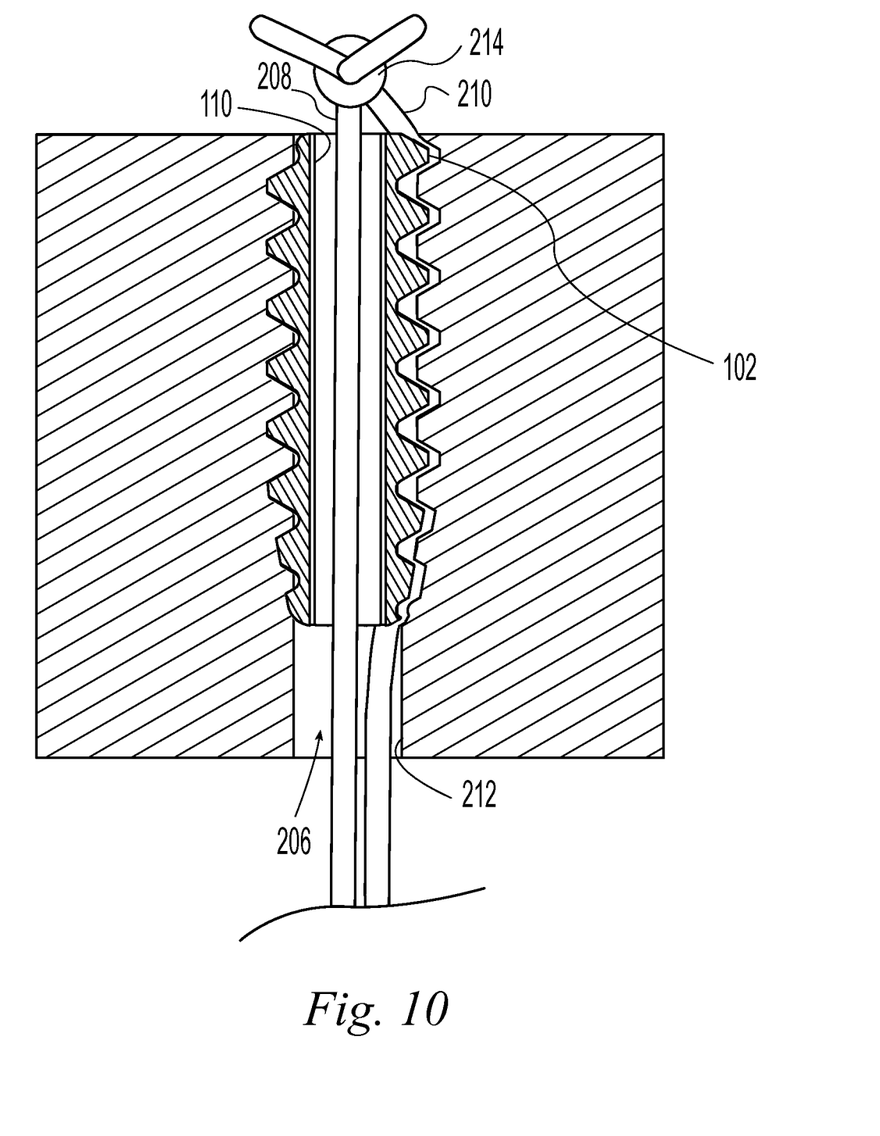
FIG. 10 is a partial sectional view illustrating a step in the method of FIGS. 8 and 9.

Referring to FIGS. 9 and 10, the threader 170 and first suture limb 208 have been withdrawn through the anchor/driver assembly 200. The anchor/driver assembly 200 is then advanced over the first limb 208 until the anchor 100 engages the opening of the bone tunnel 206. The second limb 210 may be pulled to tension it as desired before the suture anchor 100 is advanced. The anchor 100 is then advanced into the bone tunnel 206 to trap and secure the second limb 210 between the anchor body 102 and tunnel wall 212 in interference manner. The first limb 208 remains unsecured and is able to translate within the axial passage 110 of the anchor 100. The first limb 208 may be pulled to tension it as desired. The first limb may then be secured. For example, the first limb 208 may be knotted, wedged within the anchor passage 110, and/or otherwise secured. The first and second limbs 208 and 210 may be fixed together such as by tying, clamping, adhering, or by other suitable methods so that the limbs 208 and 210 are suspended over the anchor body wall. In the illustrative example of FIG. 10, the suture limbs 208 and 210 have been tied in a knot 214.

FIGS. 11 through 15 illustrate a surgical procedure for tethering two bones 300, 302 together. In the illustrative example of FIGS. 11-15, the method is used to tether two metatarsal bones of a human foot such as, for example, to correct a hallux valgus deformity.

Figure 11:
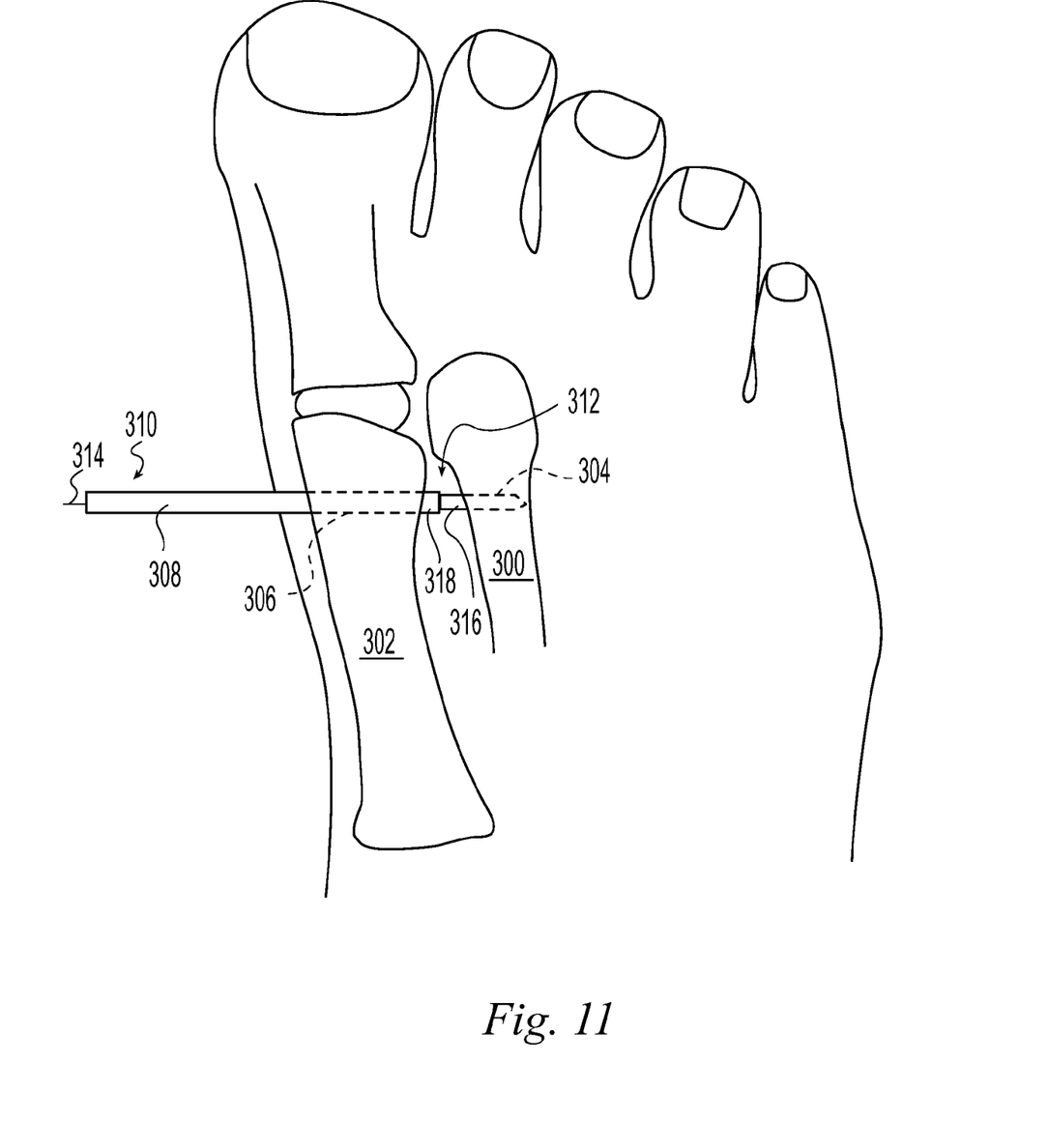
FIGS. 11-15 are cutaway views of a human foot illustrating steps in a method according to the present invention.

FIG. 11 depicts an optional step of drilling aligned first and second tunnels 304, 306 in the first and second bones 300, 302 in preparation for receiving first and second anchors. The tunnels 304, 306 may be of the same or different diameters. Alternatively, the tunnels may be omitted and the anchors may form their own tunnels in the bone. In the illustrative example of FIG. 11, a stepped drill 308 is used to form aligned tunnels with the first tunnel 304 having a diameter smaller than the second tunnel 306. The drill 308 includes an elongated body extending between a proximal end 310 and a distal end 312 along an axis 314. A first cutting portion 316 at the distal end has a first diameter and a second cutting portion 318 nearer the proximal end has a second diameter larger than the first cutting portion diameter. In the illustrative example of FIG. 11, the stepped drill 308 is advanced through the second bone 302 and into the first bone 300 to form bone tunnels 306, 304. The stepped drill 308 is then withdrawn.

Figure 12:
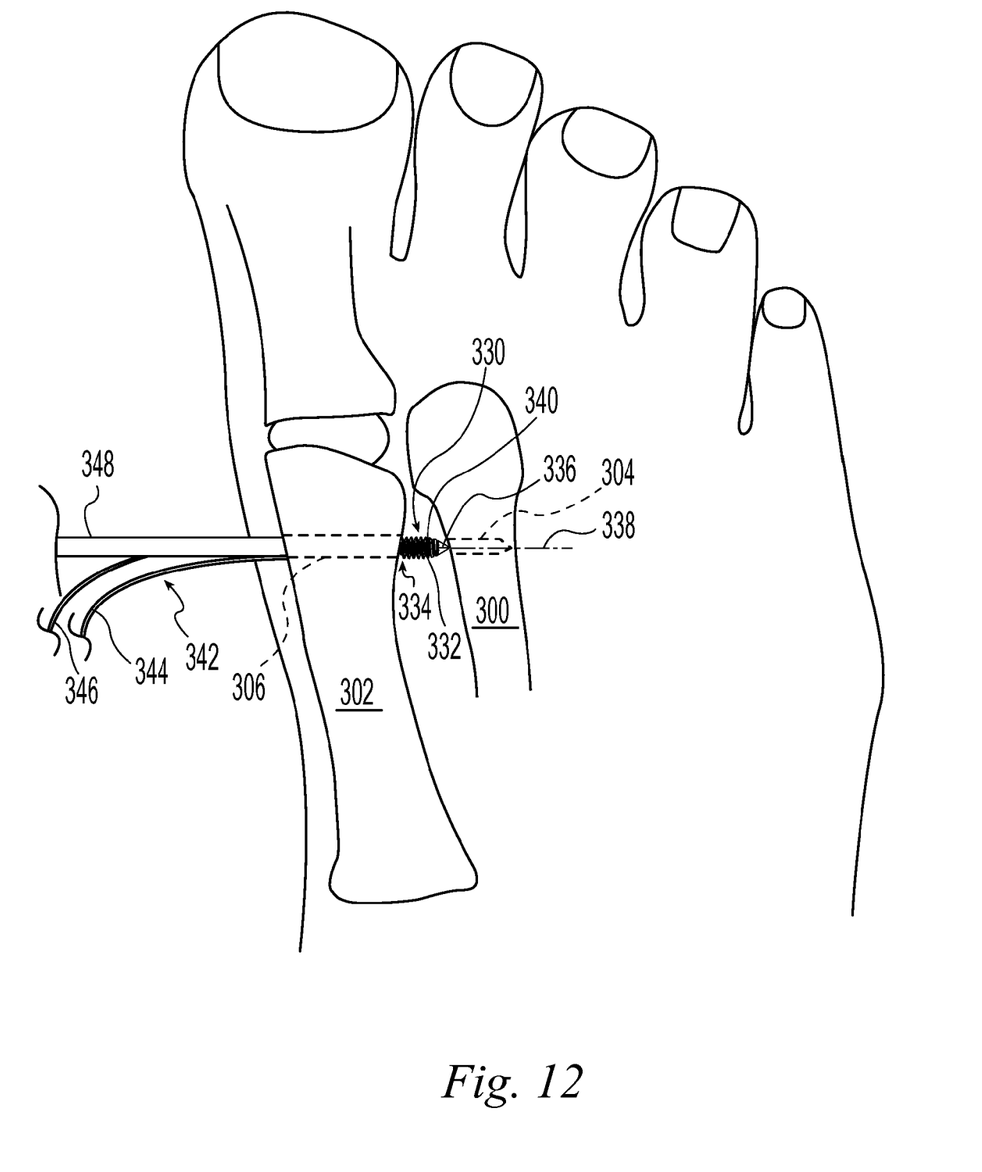
Figure 13:
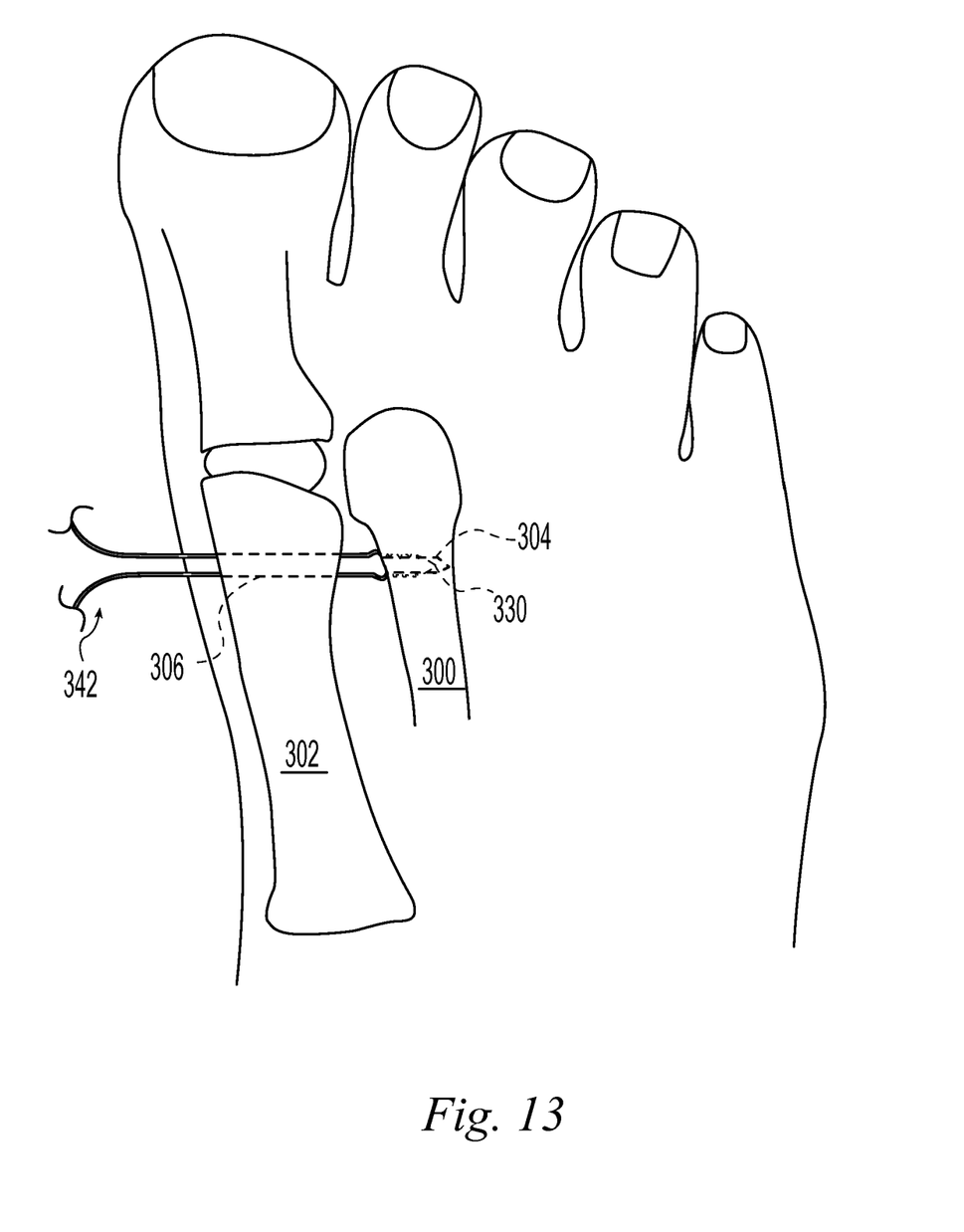

FIGS. 12 and 13 depict the step of installing a first suture anchor 330 into the first bone 300. The first suture anchor 330 has an elongated body 332 extending between a proximal end 334 and a distal end 336 along an axis 338. The first suture anchor 330 includes fixation projections 340 extending radially outwardly from the body. The first suture anchor 330 may be cannulated or non-cannulated. The first suture anchor has a suture 342 attached to it. The suture 342 may have one or more suture limbs extending from the first suture anchor 330 and the suture limbs may be fixed relative to the first suture anchor 330 to permit independent suture tensioning or they may be slidably engaged with the first suture anchor 330 so that tensioning one suture limb tensions the other. In the illustrative example of FIGS. 12-13, the first suture anchor 330 is non-cannulated and has a pointed, self tapping, distal end 336. The suture 342 includes first and second suture limbs 344, 346 fixed relative to the first suture anchor 330 to allow independent tensioning of the suture limbs. A driver 348 couples to the first suture anchor 330 to aid in installing the first suture anchor 330. In the illustrative example of FIGS. 12-13, the first suture anchor 330 is passed through the second bone tunnel 306 and is threaded into the first bone tunnel 304 to secure the first suture anchor 330 in the first bone 300 with the suture 342 extending from the first suture anchor 330 and through the second bone tunnel 306. The first suture anchor 330 may be seated proud of the first bone, flush with the first bone, or recessed within the first bone. In the illustrative example of FIG. 13, the first suture anchor 330 is seated flush.

Figure 14:
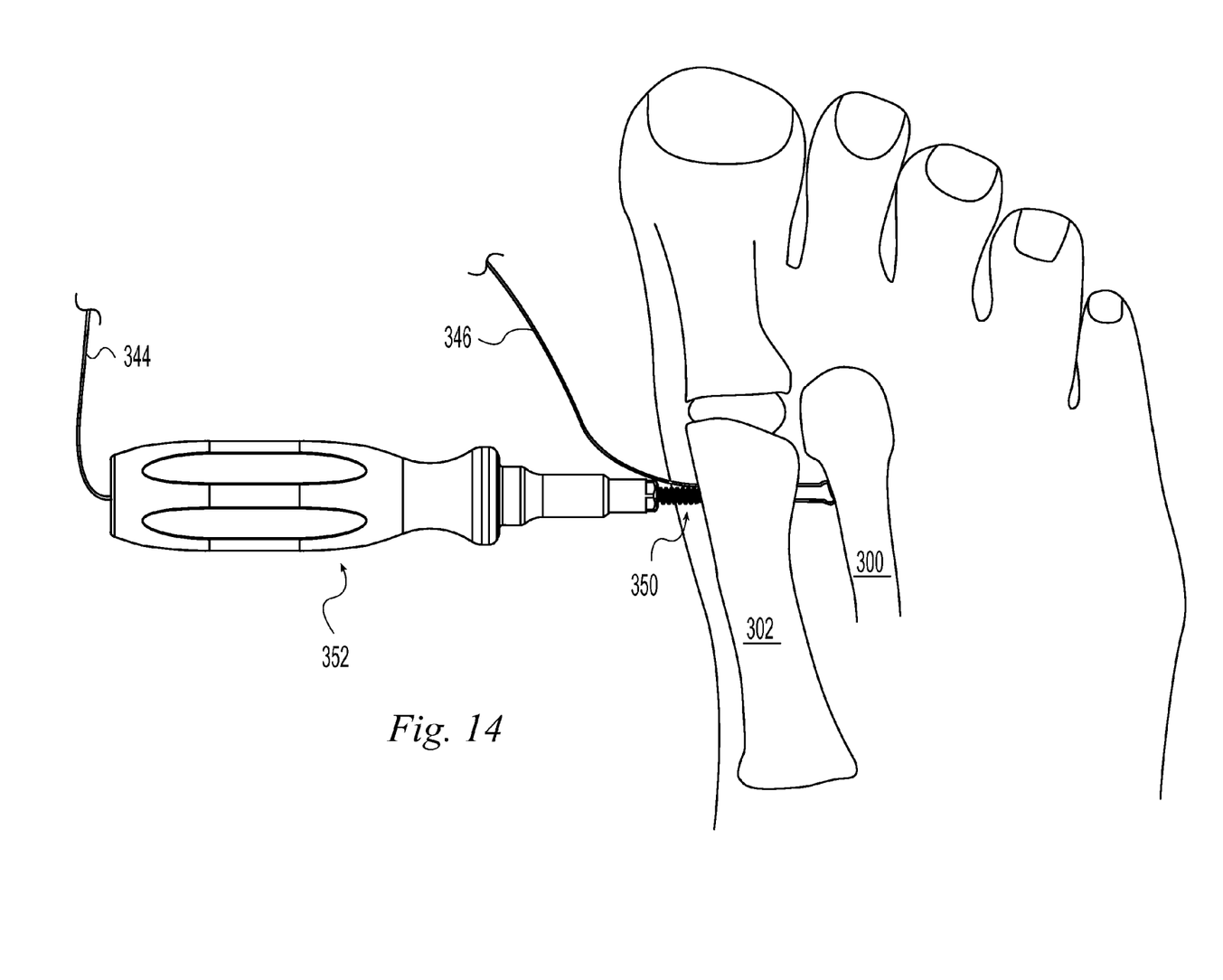
Figure 15:
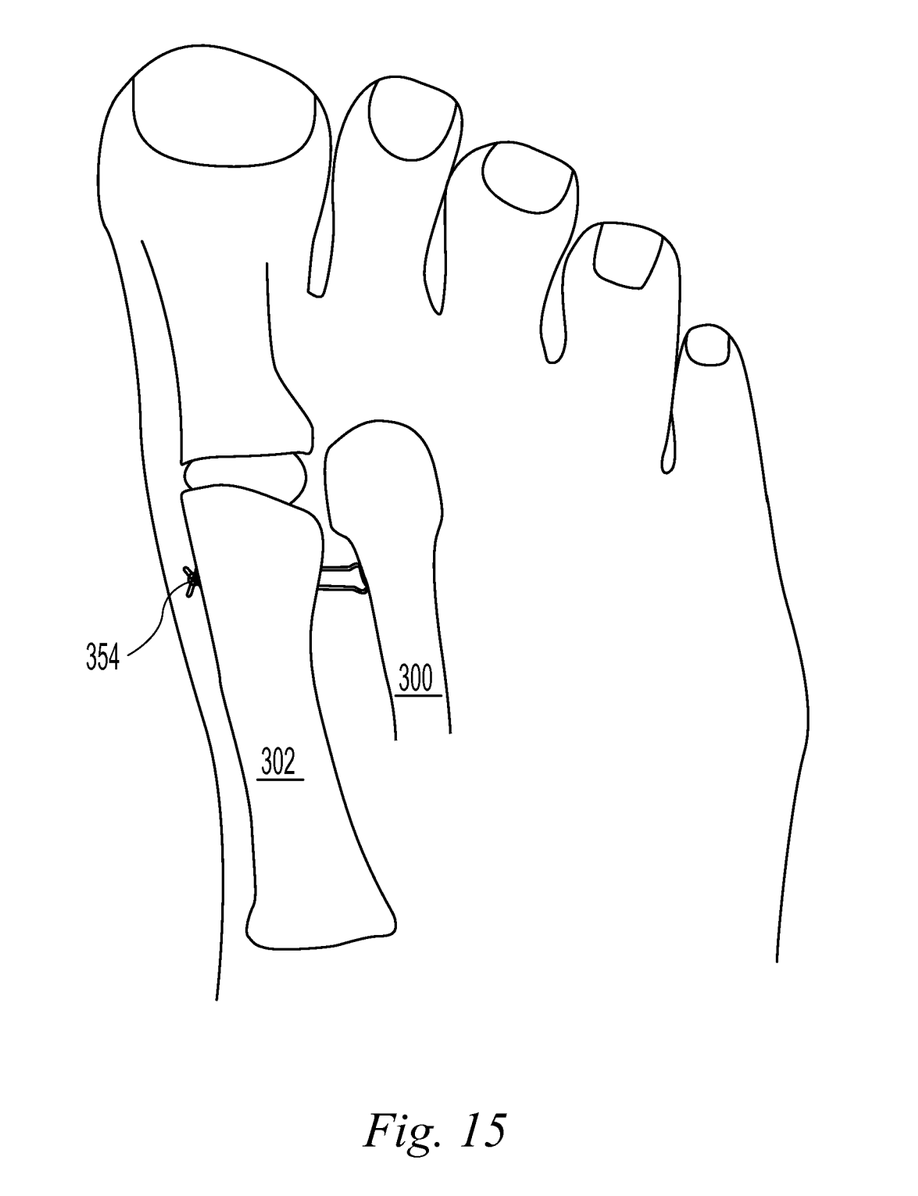

FIGS. 14 and 15 depict the steps of inserting a second suture anchor 350 into the second bone 302 and securing the suture. The second suture anchor 350 is configured like the suture anchor of FIGS. 1-4. A driver 352 is configured like the driver of FIG. 5. In the illustrative example of FIG. 14, the first limb 344 of the suture is threaded through the second suture anchor 350 and driver 352 as in the example of FIGS. 8-10. The second suture anchor 350 is then advanced over the first limb 344 until the anchor 350 engages the opening of the second bone tunnel 306. The second limb 346 may be pulled to tension it as desired before the suture anchor 350 is advanced. The anchor 350 is then advanced into the bone tunnel 306 to trap and secure the second limb 346 between the anchor body and tunnel wall in interference manner. The second suture anchor 350 may be seated proud of the second bone, flush with the second bone, or recessed within the second bone. In the illustrative example of FIG. 15, the second suture anchor 350 is seated flush. The first limb 344 remains unsecured and is able to translate within the axial passage of the second anchor 350. The first limb 344 may be pulled to tension it as desired. The suture limbs may optionally slidingly engage the first suture anchor such that pulling on the first suture limb 344 tensions both the first and second suture limb. This may be advantageous, for example, to simplify adjusting the relative position of the first and second bone while maintaining equal tension in the first and second suture limbs. The first limb may then be secured. For example, the first limb 344 may be knotted, wedged within the anchor passage, and/or otherwise secured. The first and second limbs 344 and 346 may be fixed together such as by tying, clamping, adhering, or by other suitable methods. In the illustrative example of FIG. 15, the suture limbs 344 and 346 have been tied in a knot 354.

Implants, instruments, and methods have been described to illustrate examples of the present invention. Modifications to the illustrative examples may be made within the scope of the present invention.

What is claimed is:

1. A method of securing first and second suture limbs relative to a bone, the method comprising:
    forming a bone tunnel through a portion of a bone, the bone tunnel having a first opening at a first surface of the bone and a second opening at a second surface of the bone;
    passing first and second suture limbs through the bone tunnel, the first and second suture limbs exiting together through the first opening;
    passing the first suture limb through a longitudinal cannulated of an anchor;
    inserting the anchor into the bone tunnel through the first opening to trap the second suture limb between the anchor and bone tunnel in interference relationship, the anchor having an anchor outer side surface and the bone tunnel having a tunnel wall comprised of bone, the outer side surface of the anchor engaging the tunnel wall and the second suture limb being secured between the outer side surface of the anchor and the tunnel wall, wherein the second suture limb does not pass through the longitudinal cannulation; and
    securing the first suture limb.

2. The method of claim 1 wherein securing the first suture limb comprises joining it to the second suture limb after inserting the anchor into the bone tunnel.

3. The method of claim 1 further comprising:
    passing the first suture limb through a cannulated driver engageable with the cannulated anchor;
    then tensioning the first and second suture limbs;
    then inserting the bone anchor into the tunnel with the cannulated driver.

4. The method of claim 1 further comprising:
    tensioning the second suture limb independently of the suture limb before inserting the anchor into the bone tunnel and tensioning the first suture limb independent of the second suture limb before securing the first suture limb.

5. The method of claim 1 further comprising:
after inserting the anchor into the bone tunnel, pulling the first suture limb to tension both the first and second suture limbs before securing the first suture limb.

6. A method of tethering first and second bones together, the method comprising:
anchoring a first suture anchor to the first bone;
passing first and second suture limbs from the first suture anchor through the second bone by passing the first and second suture limbs through a bone tunnel in the second bone;
passing the first suture limb through a longitudinal cannulation of a second anchor;
inserting the second suture anchor into the bone tunnel in the second bone to secure the second suture limb between the second suture anchor and bone tunnel in interference relationship, the second anchor having an anchor outer side surface and the bone tunnel having a tunnel wall comprised of bone, the outer side surface of the second anchor engaging the tunnel wall and the second suture limb being secured between the outer side surface of the second anchor and the tunnel wall, wherein the second suture limb does not pass through the longitudinal cannulation; and
securing the first suture limb.

7. The method of claim 6 wherein securing the first suture limb comprises joining it to the second suture limb after inserting the second anchor into the bone tunnel.

8. The method of claim 6 wherein the first suture anchor is generally cylindrical and has a maximum diameter along its length and the second suture anchor is generally cylindrical and has a maximum diameter along its length, the second suture anchor maximum diameter being greater than the first suture anchor maximum diameter.

9. The method of claim 6 wherein anchoring a first suture anchor to the first bone comprises passing the first suture anchor and suture through the second bone and into the first bone.

10. The method of claim 6 wherein one of the first and second suture anchors are cannulated and the other is non-cannulated.

11. The method of claim 6 further comprising:
forming aligned second and first tunnels through the second and first bones, the first bone tunnel being of a smaller diameter than the second bone tunnel.

12. The method of claim 11 wherein the tunnels are formed in a single action with a stepped drill.

13. The method of claim 6 wherein the first and second suture ends are fixed to the first suture anchor and are independently tensionable, the method further comprising:
tensioning the second suture limb independent of the first suture limb before inserting the anchor into the bone tunnel and tensioning the first suture limb independent of the second suture limb before securing the first suture limb.

14. The method of claim 6 further comprising:
after inserting the second suture anchor into the second bone tunnel, pulling the first suture limb to tension the first and second suture limbs before securing the first suture limb.

15. The method of claim 14 wherein the first and second suture ends slidingly engage the first suture anchor, such that after the first suture anchor is fully installed, pulling on one of the first and second suture ends causes the other of the first and second suture ends to slide relative to the second suture anchor.

16. The method of claim 6 wherein the bones are metatarsal bones of the human foot.

* * * * *